United States Patent [19]

Renzel et al.

[11] 4,210,904

[45] Jul. 1, 1980

[54] METHOD AND APPARATUS FOR CONVERTING ANALOG ULTRASONIC ECHO SIGNALS INTO DIGITAL FORM

[75] Inventors: Peter Renzel, Duren; Werner Vermoehlen, Elsdorf, both of Fed. Rep. of Germany

[73] Assignee: Krautkramer-Branson, Incorporated, Stratford, Conn.

[21] Appl. No.: 941,378

[22] Filed: Sep. 12, 1978

[51] Int. Cl.² .......................................... H03K 13/02
[52] U.S. Cl. ........................ 340/347 AD; 340/347 M; 364/507; 367/74; 369/113
[58] Field of Search .................... 364/472, 487, 507; 328/28; 340/347 M, 347 AD, 347 NT, 1 R, 1 C, 3 C; 343/5 DP, 5 PC; 73/600

[56] References Cited

U.S. PATENT DOCUMENTS

| | | | |
|---|---|---|---|
| 2,994,825 | 8/1961 | Anderson | 340/347 NT X |
| 3,662,380 | 5/1972 | Cargile | 340/347 M X |
| 3,909,771 | 9/1975 | Pickering et al. | 340/1 R |
| 3,914,760 | 10/1975 | Logue | 340/347 M X |
| 3,981,184 | 9/1976 | Matay | 364/472 X |

Primary Examiner—Thomas J. Sloyan
Attorney, Agent, or Firm—Ervin B. Steinberg; Philip J. Feig

[57] ABSTRACT

A method and apparatus are provided for converting into digital form the analog ultrasonic echo signals received as a result of cyclically transmitted ultrasonic search signals intercepting an acoustic discontinuity in a workpiece. The ultrasonic echo signals are divided into a discrete number of raster-like scan lines which are scanned electronically by a microprocessor. Digital signals are generated for each line of the raster-like scan and such signals assume either a first or second state along the scan line in accordance with the signal amplitude along that line. As successive scans are made at progressively higher amplitudes of the echo signal, the amplitude required for varying the digital signal between the states for a particular scan line is incrementally increased with each scan line. A comparator receives at a first input the echo signals and at a second input a signal from a digital-to-analog converter whose output is incrementally increased on successive scan lines by the microprocessor. The outputs of the comparator are placed into storage in the microprocessor.

19 Claims, 4 Drawing Figures

METHOD AND APPARATUS FOR CONVERTING ANALOG ULTRASONIC ECHO SIGNALS INTO DIGITAL FORM

BACKGROUND OF THE INVENTION

This invention relates to ultrasonic nondestructive testing of workpieces, and more particularly for converting analog utrasonic echo signals arising from ultrasonic search signals intercepting an acoustic discontinuity in a workpiece into digital signals which may be stored.

In pulse-echo ultrasonic testing of materials an electro-acoustic transducer, for example a piezoelectric transducer, acoustically coupled to a workpiece transmits ultrasonic search signals into such workpiece. When the search signal intercepts an acoustic discontinuity, such as the entrant or rear will surface of the workpiece or an acoustic discontinuity disposed in the workpiece, a portion of the signal is reflected back toward the transducer. The reflected ultrasonic signals from the workpiece, which commonly are referred to as ultrasonic echo signals, are received by the electro-acoustic transducer and transformed into electrical signals. By comparing the amplitudes of two or more successive echo signals and the time differences between these signals, or by comparing the echo signals with signals received from a reference defect, data is provided for analyzing the workpiece under test. A common method of displaying or illustrating the instantaneous values of the echo signals is to provide an A-scan representation on the screen of a cathode ray tube, which display is an amplitude versus time presentation. In order to compare data from ultrasonic echo signals with data obtained from a reference workpiece or to compare a signal received at different times from the same workpiece, or to compare signals received from different locations in the workpiece, the cathode ray tube A-scans must be stored, for example, in a computer. The computer, in turn, may be preprogrammed for analyzing the data from the workpiece under test. Since the signal displayed on the screen is in analog form, it must first be converted into a digital form suitable for storage.

A common method presently employed for processing the analog A-scan data to derive a digital form is the "sample-and-hold" method which will be explained hereinafter in connection with the present invention, and which method is described in "Elektronik", 1975, Vol. II, pages 85–86 and Vol. III, pages 105–106, published by Fransis-Verlag, Munich. The sample-and-hold method requires a large number of sequential samples in order to obtain good resolution of the echo signal. Of course, the larger number of samples requires longer processing and storage time.

Accordingly, it is an object of this invention to provide a novel method and apparatus for converting analog ultrasonic echo signals into digital form exhibiting substantially faster response time without loss of resolution and without increasing the repetition rate of the ultrasonic test system employed.

A further object of this invention is to provide a new and improved method and apparatus for converting analog ultrasonic echo signals into digital form in a manner to save processing and storage time.

SUMMARY OF THE INVENTION

In carrying out this invention in one illustrative form thereof, ultrasonic echo signals arising from acoustic discontinuities in the workpiece are digitized along a discrete number of lines in a raster-like scan, such lines varying according to the signal amplitude. A digital signal is generated for each line of the raster-like scan corresponding to predetermined amplitude levels. The digital signal assumes either a high state or low state along the scan line responsive to the amplitude of the echo signal when compared with the predetermined reference amplitude associated with the respective scan line. As each line is successively scanned, the amplitude required for varying the digital signal between both states for that particular scan line is incrementally increased. Digital signals derived in this manner are stored in a suitable storage means, such as a computer. The terms "high state" and "low state" in the preferred embodiment disclosed hereafter refer to the output logic levels associated with conventional digital circuits.

DESCRIPTION OF THE PREFERRED EMBODIMENT

Figure 1:
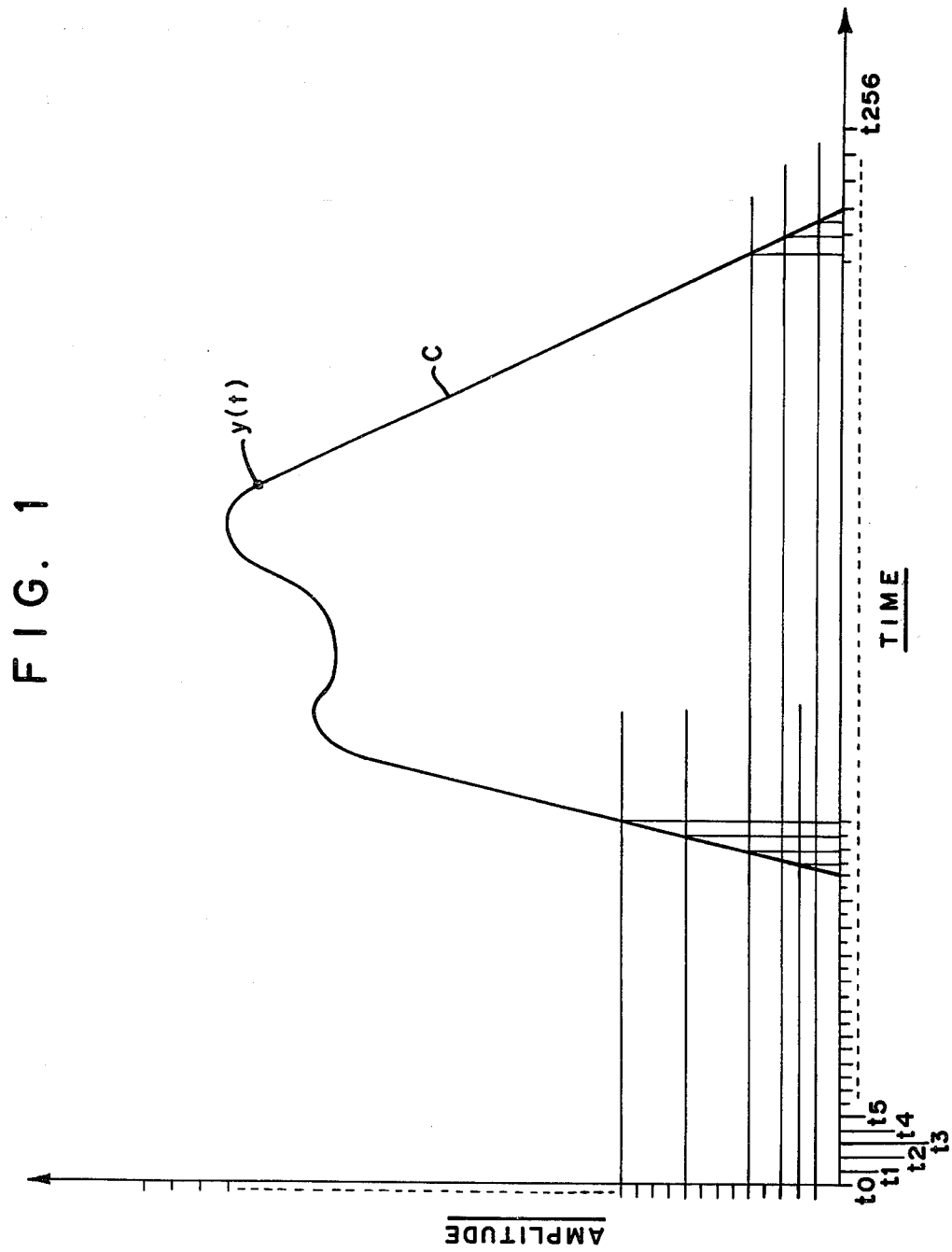
FIG. 1 is a graphic representation of an A-scan amplitude versus time of an echo signal illustrating analog-to-digital conversion utilizing a sample-and-hold method.

Before entering into a discussion of the present invention the prior art sample-and-hold method of analog-to-digital conversion of an echo signal will be explained. First, a trigger pulse is applied to an electroacoustic transducer causing an ultrasonic search signal to be transmitted into a workpiece. This signal is reflected from an acoustic discontinuity, such as the entrant surface or rear wall of the workpiece and/or a flaw or defect disposed within the workpiece, and the reflected ultrasonic echo signals are received by the same or a second electroacoustic transducer and converted into electrical signals. In FIG. 1, one such signal is displayed as an A-scan on a cathode ray tube screen, as curve "y(t)", or curve C, which curve is a function of the amplitude versus time of the reflected or echo signal reflected from the acoustic discontinuity. In accordance with the sample-and-hold method of analog-to-digital conversion, the time or t-axis (abscissa) and the amplitude or y-axis (ordinate) are subdivided in incremental raster-like divisions, with one raster division corresponding to one bit of a bit storage means of a computer. In pulse-echo ultrasonic nondestructive testing the t-axis corresponds to the distance that the ultrasonic signal travels in accordance with the following equation:

$$S = S_v + C_p \times t_p$$

wherein
S = total distance traveled from the transducer to the acoustic discontinuity and back to the transducer;

$S_v$ = twice the delay path from the transducer to the surface of the workpiece;

$C_p$ = second propagation velocity of the workpiece, and $t_p$ = ultrasonic signal travel time in the workpiece.

Due to the travel time of the ultrasonic signal, for practical applications the time axis is generally subdivided into 256 bits or raster-like divisions while the signal amplitude or phase data of the signals along the y or amplitude axis is divided into 64 bits or raster-like divisions.

As is illustrated on the time axis of FIG. 1, when the first pulse is triggered by the ultrasonic system, the first interval $\Delta t_1 = t_1 - t_0$ is established on the time axis and $y(\Delta t_1)$ is sampled and stored. As the second pulse is triggered, the interval $\Delta t_2 = t_2 - t_1$ is established, and the amplitude of curve C is again sampled and stored. This process continues for 256 successive sample-and-hold steps. Assuming the triggering of one pulse each 1/200th of a second, the sample-and-hold process requires $256 \times 1/200$ seconds = 1.28 seconds, which is the time required to completely convert to digital form one A-scan or curve C. Accordingly, a minimum cycling time of 1.28 seconds is required for practical testing to provide a digital representation of curve C. That is, the analog data represented by curve C must remain constant for an entire sampling period of 1.28 seconds during which time there can be no relative motion between the transducer and the workpiece.

In accordance with the present invention, a method is provided for producing a digital signal in a substantially reduced time without sustaining a decrease in signal resolution for both the amplitude and time axes and without increasing the repetition rate of the triggered pulses. This is achieved in the present invention by dividing the amplitude or y-axis of the curve C illustrated in FIG. 2a into lines in a raster-like pattern instead of the heretofore described division of the time or t-axis. Digital signals are generated for each scan line of the raster-like pattern, which signal either assumes a first state or level or a second state or level along the scan line in accordance with the echo signal amplitude along that line. The reference level for establishing the output first and second levels on a given scan line is incrementally increased by one increment 8bit) in amplitude for each subsequent scan line. The output digital signal levels are determined by a voltage comparator which has a reference level applied to one of its inputs and the echo signal applied to the other input. The digital signal generated for each scan line assumes the first level when the signal amplitude of the echo signal exceeds the reference level, and the digital signal assuming the second level when the echo signal amplitude is less than the reference level. In the preferred embodiment, when the echo signal exceeds the reference level the output digital signal assumes the high level and when the echo signal is less than the reference level the digital signal assumes the low level. For each successive scan line the reference signal level is increased by one increment, which is 1/64 of the 64 scan line levels forming the amplitude or y-axis. The output signal from the comparator for each scan line is placed in storage, with the digital signal levels being added synchronously in time increment responsive relation to those of the first and preceding scan lines which have previously been placed in storage. The process is continued until the last raster line has been scanned. The echo signal may then be recreated by simple digital to analog conversion of summed digital level signals established along the time base in accordance with the above-described technique.

Figure 2A:
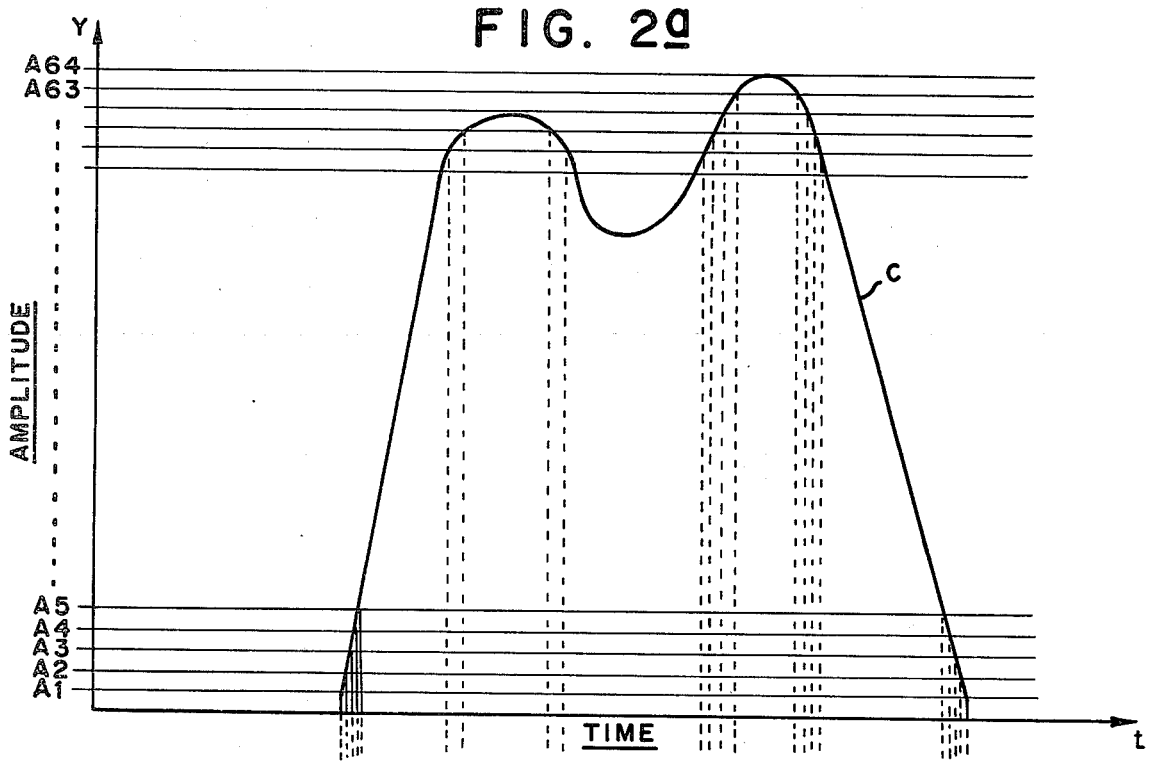
FIGS. 2a and 2b illustrate the analog-to-digital conversion of an echo signal in accordance with the present invention.
Figure 2B:
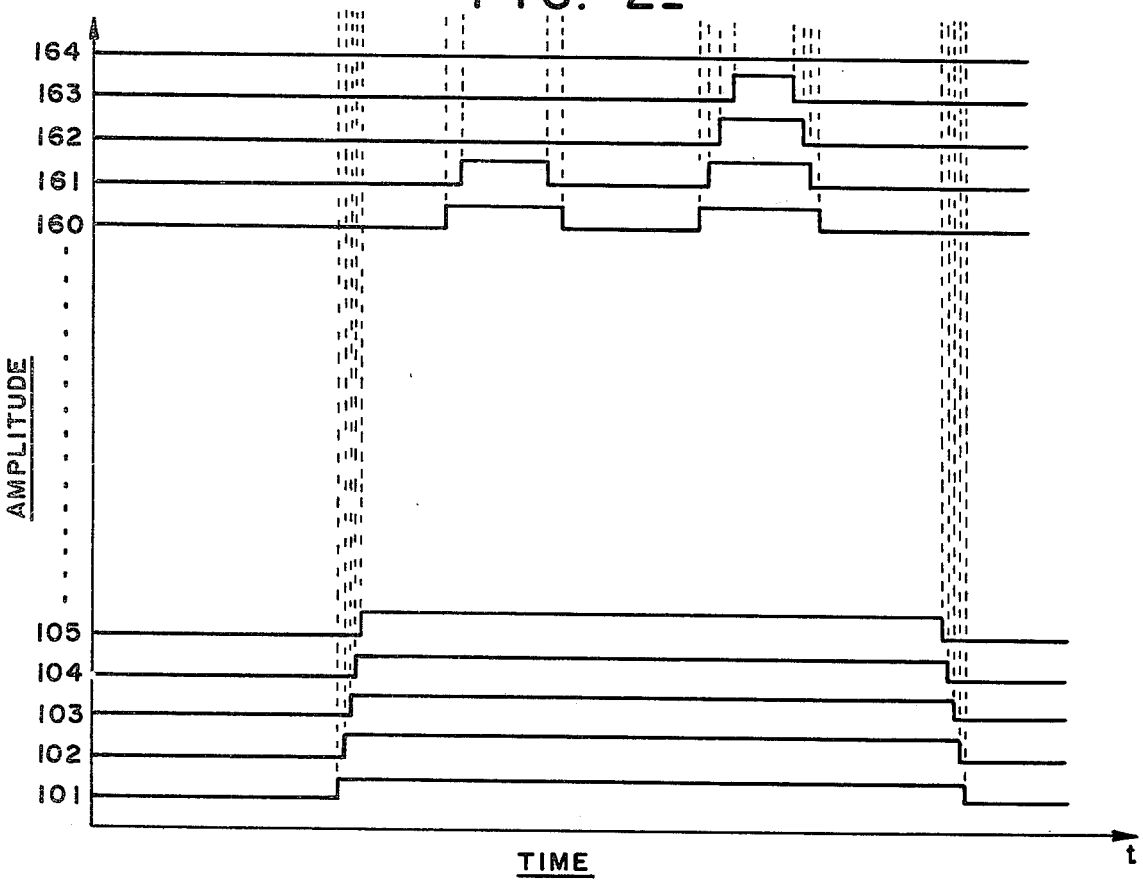

This technique is more clearly illustrated in FIG. 2b which illustrates digital signals 101 through 105 and 160 through 164, corresponding to the digital signals which are generated in accordance the method of this invention from the echo signal curve C shown in FIG. 2a. As seen in FIG. 2a, the curve C occupies the entire range of the amplitude or y-axis, i.e. the entire 64 bits (or scan line amplitudes), each of which scan line will have a digital signal associated therewith placed in storage. Accordingly, digital signal 101 is generated during the first scan line $A_1$; signal 102 is generated during the second line $A_2$; signals 103, 104 and 105 are generated during scan lines $A_3$ through $A_5$, and so on, with signals 160 through 164 being generated during scan line $A_{60}$ through $A_{64}$. The amplitudes required for determining the high and low levels of individual signals in these scans are raised one increment for each scan line, thereby requiring the echo signal amplitude during succeeding scan lines to be greater in order for the digital signals generated by the comparator circuit to assume the high level. The digital signals represented in FIG. 2b are generated during successive cycles corresponding to each scan line within individual time periods or bits along the time axis which are added in the computer so that the new digitized curve C in either the t or y coordinate is stored in either the high or low level in the storage means. By synchronously summing the signals 101 through 164 in time increment responsive relation, curve C of FIG. 2a may be recreated for analysis purposes.

With the present method, the length of the time axis does not govern the time required for processing and storing the digital data. The maximum time for storing the echo signal represented by curve C, in the worst case, cannot be more than the entire amplitude range of the y-axis subdivided into 64 bits (or scan lines). Accordingly, the maximum storage time of $64 \times 1/200$ seconds = 0.32 seconds, as compared with the 1.28 seconds required for the sample-and-hold method which employs a 256 bit division (increment) along the times axis. If the maximum amplitude of the echo signal examined is only a fraction of the 64-bit amplitude or y-axis, the time required for storing would be reduced further in accordance with that fraction as described hereinafter. Accordingly, the storage time required by the present method is, in the worst case, at most only one quarter of that required by the sample-and-hold method.

Figure 3:
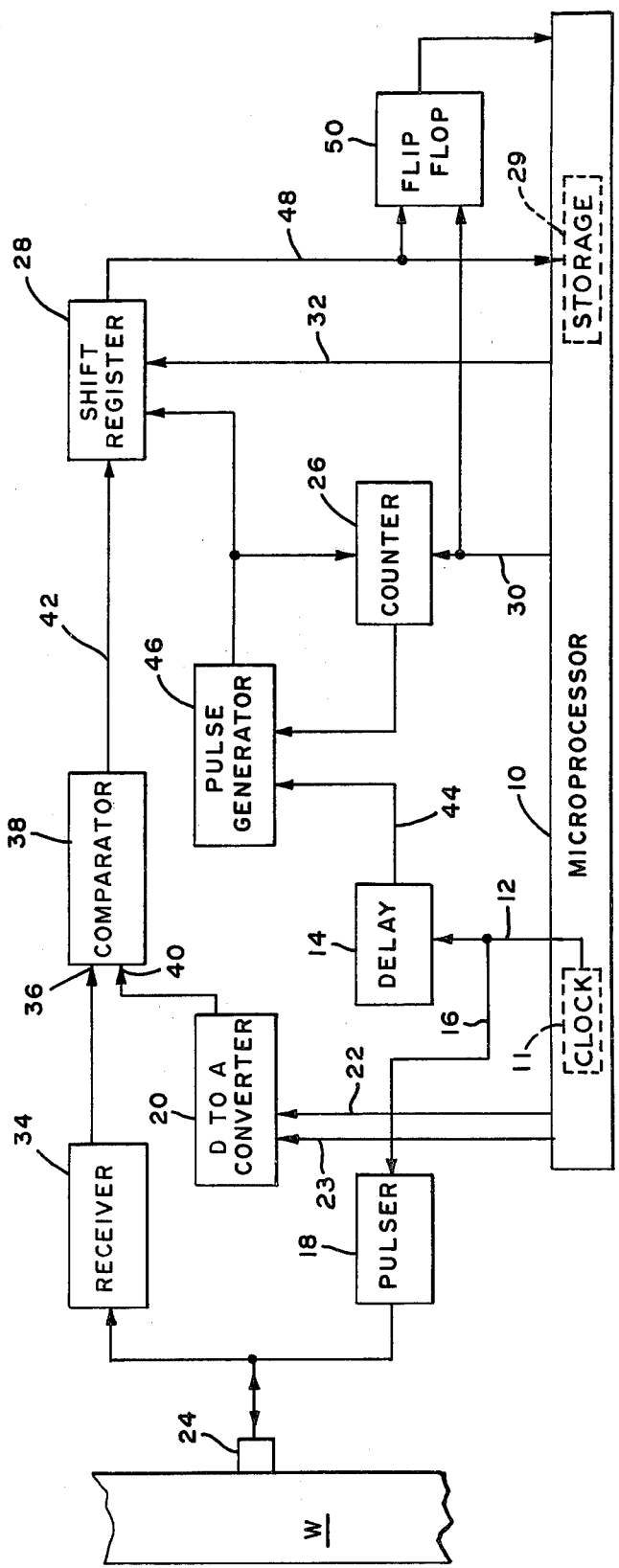
FIG. 3 is a block diagram of a preferred embodiment of an electrical circuit for implementing the analog-to-digital conversion method illustrated in FIGS. 2a and 2b.

FIG. 3 is an electrical circuit block diagram illustrating a preferred embodiment of an apparatus for practising the method of analog to digital conversion in accordance with the present invention. A microprocessor 10 including a storage means contains a clock 11 which provides clock start pulses via conductor 12 to a pulse delay circuit 14 and a trigger signal via conductors 12 and 16 to a pulse generator 18. The microprocessor 10 also delivers a reset pulse to a digital-to-analog converter 20 via conductor 22. The reset pulse sets the output voltage level of the converter 20 initially to the lowest predetermined (base) reference level. For each ensuing pulse generator signal applied to the transducer 24, the output voltage level of the digital-to-analog converter 20 is incrementally increased bit by bit via a signal along conductor 23 for the 64 cycles of scan lines to the maximum measurement range of the amplitude or y-axis. Reset pulses are also applied from the microprocessor 10 to a counter 26 and a shift register 28 via conductors 30 and 32 respectively. The pulse generator 18 responsive to the receipt of the trigger pulses along conductors 12 and 16 energizes the transducer 24 at the system pulse repetition rate, for instance 200 Hz. The transducer, coupled to a workpiece W via a suitable couplant, such as water or oil, cyclically applies an ultrasonic search signal to the workpiece W which signals are reflected by acoustic discontinuties and received by the transducer 24 as ultrasonic echo signals. The transducer 24 converts the ultrasonic echo signals into electric analog signals which are applied to a receiver 34. The output signals from the receiver 34, which are referred to as the "echo signals", are applied to one input terminal 36 of a comparator 38. The output reference level voltage from the digital-to-analog converter 20 is applied to the other input terminal 40 of the comparator 38. The comparator 38 compares the analog echo signals from the receiver 34 with the amplitude of the reference level supplied from the digital-to-analog converter 20. If the amplitude of the echo signal exceeds the reference level from the digital-to-analog converter 20, the output of the comparator 38 assumes a first state (the high level). The output digital signal on conductor 42 assumes a second state (the low level) when the amplitude of the echo signal from the receiver 34 has an amplitude which is lower than that of the reference voltage level from the digital-to-analog converter 20. The output of the comparator 38 is applied via conductor 42 to a shift register 28 where the signal is digitized as explained hereafter.

The delay pulse generator 14 generates on conductor 44 a gate start signal at a predetermined time after receipt of a clock start pulse from the microprocessor 10 on conductor 12. The gate start signal on conductor 44 defines the start of the time interval during which the echo signal applied to the comparator 38 is divided into increments. The delay pulse generator 14 is generally adjusted to start the time interval commensurate with the anticipated receipt of echo signals from the workpiece. Each signal on conductor 44, associated with a respective search signal, is applied to a high frequency pulse generator 46 for starting the generation of high frequency clock pulses which are applied to the shift register 28. The clock pulses from the high frequency generator 46 may be of a frequency up to 80 MHz, which frequency is much greater than the pulse repetition rate at which pulse generator 18 is operated (200 Hz). The clock pulses control entry of the digital signals provided from comparator 38 along conductor 42 into the shift register 28. That is, the instantaneous output signal from comparator 38 is sampled and fed into the shift register 28 upon the occurrence of each clock pulse from pulse generator 46. Accordingly, shift register 28 is controlled responsive to the receipt of the clock pulses from the high frequency generator 46 and will shift, for example, up to 256 bits (time increments) at the high frequency rate. The clock pulses from the high frequency generator 46 are also applied to the counter 26. The counter 26 provides a count which is dependent upon the predetermined quantity of bits to be shifted by the shift register 28, in the present example 256 counts. When the predetermined quantity is reached, the counter 26, which is also coupled to the high frequency generator 46, inhibits any further clock pulses from the high-frequency generator 46. The time interval between the gate start signal and the inhibiting of any further clock pulses from the high frequency pulse generator 46 is referred to as a gated time interval. Accordingly, the shift register 28 can handle 256 bits of data (predetermined time increments) for each scan line which quantity of bits is controlled by the pulse generator 46 and the counter 26. The frequency of the clock pulses generated by the high frequency pulse generator therefore depends upon the desired resolution for the time base of the analog echo signal. The shift register 28 has its output coupled through conductor 48 to the storage means 29 in the microprocessor 10 and also to a flip flop circuit 50.

Referring again to FIGS. 2a and 2b, echo signals applied to the terminal 36 of comparator 38 are compared with the reference levels set by the voltage at terminal 40 of the comparator 38 provided by the digital-to-analog converter 20, which initially is at the amplitude of the first cycle, or scan line, $A_1$. The microprocessor 10 causes the contents of the shift register 28 corresponding to scan line 101 to be placed bit by bit into a special accumulator register (not shown) and adds the contents of this register bit by bit to the corresponding byte of storage means 29 in the microprocessor 10. In the present example 256 such bytes are provided. The storage means is reset to zero before the first trigger pulse for generating digital signal 101 is provided via conductors 12 and 16 to pulser 18. Likewise digital-to-analog converter 20 and counter 26 are reset by signals along conductors 22 and 30 respectively.

After storing each bit of scan line 101 in microprocessor 10 counter 26 will be readied for the next cycle by a reset pulse via conductor 30. The reference level from the digital-to-analog converter 20 at terminal 40 is incrementally increased from level $A_1$ to $A_2$ by the signal along conductor 23 from microprocessor 10. The next trigger pulse gnerates the next scan line 102 and the microprocessor sums the new scan line 102 to scan line 101 in time increment responsive relationship according to its position in the 256 bits in the shift register 28. This process is repeated 64 times if the amplitude of the electrical echo signal encompasses the entire y-axis. As previously pointed out, the reference level appearing at terminal 40 of the comparator 38 is incrementally increased with progressively increasing amplitudes corresponding to each line designated 1 through 64. Upon completion of a complete scan of 64 cycles, the curve C amplitude, which has been divided into discrete bit counts, is available from the storage means of the microprocessor 10 for use at a subsequent time for comparison or evaluation purposes with other echo signals or reference signals to determine the nature and character of the defect in the workpiece being examined.

In order to avoid unnecessary counting and storage up to the 64th scan line of the echo signal when the amplitude of that signal does not exceed the reference voltage level of the 63rd or any lower scan line, the amplitude level provided at input 40 of comparator 38 by the digital-to-analog converter 20 is increased only when the echo signal applied from the receiver 34 is of sufficient amplitude to exceed the reference level at terminal 40 of the comparator 38 during the preceding scan cycle. When the amplitude fails to exceed the reference level, that is, when high level signals are absent at the output of comparator 38 during one entire scan cycle, the flip flop circuit 50 is not set, causing the microprocessor 10 to stop the storing process. The shift register 28 is reset via a signal provided along conductor 32 from the microprocessor 10, and the counter 26 is reset via a signal along conductor 30 from the microprocessor. Moreover, the digital-to-analog converter 20 is reset to its base value rather than increased by one bit or reference level increment in order to commence scanning of a new echo signal.

By way of example only, circuit components and their manufacturers suitable for use in the illustrated embodiment of the present invention are as follows:

Microprocessor 10—Z80, Mostek/Zilog.
Counter 26,—MC10178, Motorola, Inc.
Digital-to-Analog Converter 20—ZN425, Ferrant, or SN 72741, Texas Instruments, Inc.
Pulse Delay Generator 14—74LS221, Texas Instruments, Inc.
Comparator 38—MC1651L, Motorola, Inc.
High Frequency Pulse Generator 46—MC1658, MC10178, Motorola, Inc.
Shift Register 28—MCM10147, MC10178, Motorola, Inc.

It will be apparent that the above described apparatus functions equally as well when the reference level is initially at its maximum amplitude and incrementally decreased. Moreover, it is possible to preprogram the microprocessor in a manner for causing the digital-to-analog converter to provide reference levels within a predetermined amplitude range or ranges for digitizing a particular portion of the echo signal such as the peak or dip.

The method and apparatus of the present invention enables an ultrasonic analog echo signal to be quickly digitized into a digital data signal and stored. Electronic scanning and the generation of digital signals along a raster line scan which scans the analog signal at progressively greater amplitudes provide increased processing and storage speed without sustaining any loss of resolution in either the amplitude or the time base of the signal and without increasing the test repetition rate. The described method and apparatus also reduce the time which would otherwise be required by the unnecessary counting and storing when there is no digital signal being generated from the ultrasonic echo signal received from the workpiece.

Since other changes and modifications, varied to fit particular operating requirements and environments, will be apparent to those skilled in the art, the invention is not considered limited to the example chosen for purposes of disclosure, and covers all changes and modifications which do not constitute departures from the true spirit and scope of this invention which shall be limited solely by the scope of the appended claims.

What is claimed is:

1. A method for processing and storing an echo signal in pulse-echo ultrasonic testing comprising the steps of:
    cyclically transmitting ultrasonic search signal into a workpiece;
    receiving corresponding ultrasonic echo signals, each echo signal being responsive to a respective search signal intercepting an acoustic discontinuity in the workpiece and converting each such echo signal into an electrical analog echo signal;
    generating a reference signal and varying the amplitude level of said reference signal from an initial value by a predetermined increment concomitantly with each cyclically transmitted ultrasonic search signal until a predetermined condition is reached;
    providing a signal indicative of a gated time interval commencing a predetermined time after transmitting each search signal and terminating after a predetermined quantity of time increments occurs;
    comparing the amplitude of a cyclically received analog echo signal with the amplitude level of a respective reference signal and generating a digital signal responsive to the amplitude of said electrical analog signal exceeding or failing to exceed the amplitude level of said reference signal at predetermined time increments during a gated time interval, and
    storing said digital signals so generated in time increment responsive relation.

2. The method as set forth in claim 1, including the step of resetting the amplitude level of said reference signal to its initial value when said predetermined condition is reached.

3. The method as set forth in claim 2, said predetermined condition occurring after a predetermined quantity of reference signal amplitude levels has been established.

4. The method as set forth in claim 2, said predetermined condition being the generating of a digital signal indicating that a respective analog signal failed to exceed the amplitude level of one of said reference signals during a gated time interval.

5. The method as set forth in claim 1, and summing said stored signals in time increment responsive relation.

6. The method as set forth in claim 1, said initial value of the amplitude level of said reference signal being a base value and said varying the amplitude level being increasing the amplitude level incrementally.

7. The method as set forth in claim 1, said initial value of the amplitude level of said reference signal being a maximum value and said varying the amplitude level being decreasing the amplitude level incrementally.

8. An apparatus for converting analog ultrasonic echo signals received from a workpiece into digital signals for storage including means for cyclically transmitting ultrasonic search signals into a workpiece and receiving in response thereto ultrasonic echo signals, each echo signal being responsive to a respective search signal intercepting an acoustic discontinuity in the workpiece and converting each such echo signal into an electrical analog echo signal wherein the improvement comprises:
    means for producing a reference signal and varying the amplitude level of said reference signal from an initial value by a predetermined increment concomitantly with each cyclically transmitted search signal until a predetermined condition is reached;
    means coupled to said means for transmitting for providing a signal defining a gated time interval commencing a predetermined time after transmitting each search signal and terminating after a predetermined quantity of time increments occurs;
    means for generating a digital signal coupled for receiving said signal defining a gated time interval, said reference signal and said echo signals and providing a digital signal for each reference signal indicative of the condition whether the amplitude of a respective electrical analog echo signal exceeds or fails to exceed the amplitude level of said reference signal at predetermined time increments during a gated time interval, and
    means storing coupled for receiving said digital signals and storing said digital signals in time increment responsive relation.

9. An apparatus as set forth in claim 8, said means for producing a reference signal including resetting means coupled for providing a reset signal when said analog signal fails to exceed the amplitude level of a respective reference signal during said predetermined time increments.

10. An apparatus as set forth in claim 8, said initial value being a base level and said varying the amplitude level comprising means for increasing said level incrementally.

11. An apparatus as set forth in claim 8, said initial value being a maximum level and said varying amplitude level comprising means for decreasing the level incrementally.

12. An apparatus as set forth in claim 8, said means for providing a signal defining a gated time interval comprising:
   delay means coupled to said means for transmitting for providing a gate start signal commencing a predetermined time after transmitting each search signal;
   pulse generating means coupled to said delay means for providing high frequency clock pulses commencing upon receipt of said gate start signal, and
   counting means coupled to said pulse generating means for counting the quantity of clock pulses and providing an inhibit signal to said pulse generating means for stopping said clock pulses when said counted quantity of clock pulses reaches a predetermined value, the time interval between said gate start signal and said inhibit signal defining a gated time interval.

13. An apparatus as set forth in claim 12, said means for generating a digital signal comprising:
   comparing means coupled for receiving said reference signal and said electrical analog echo signal and providing a digital signal for each reference signal indicative of the condition whether the amplitude of a respective electrical analog echo signal instantaneously exceeds or fails to exceed the amplitude level of said reference signal, and
   shift register means coupled to said comparing means and to said pulse generating means for receiving said digital signal and sampling and shifting such digital signal commensurate with its instantaneous condition in response to the receipt of each clock pulse, thereby providing said digital signal in predetermined time increments during a gated time interval.

14. An apparatus as set forth in claim 13, said means for storing including a microprocessor coupled to said shift register means for receiving said digital signals and storing each digital signal in time increment responsive relation.

15. An apparatus for converting ultrasonic echo signals received from a workpiece into digital signals for storage including clock means for cyclically providing trigger signals; transmitting means coupled to said clock means for transmitting ultrasonic search signals into a workpiece responsive to receipt of said trigger signals; receiving means coupled for receiving ultrasonic echo signals responsive to a respective search signal intercepting an acoustic discontinuity in the workpiece and converting each such echo signal into an electrical analog echo signal wherein the improvement comprises:
   reference signal generating means for establishing a reference signal having an amplitude level and varying the level from an initial value by a predetermined increment concomitantly with each cyclically transmitted search signal until a predetermined condition is reached;
   comparing means coupled to said receiving means and said reference signal generating means for receiving said analog echo signal and said reference signal and providing an output signal indicative of said analog signal instantaneously exceeding or failing to exceed the amplitude level of said reference signal;
   delay means coupled to said clock means for providing a gate start signal at a predetermined time after each trigger signal;
   pulse generator means coupled to said delay means for providing high frequency clock pulses responsive to said gate start signal;
   counter means coupled to said pulse generator means for counting the quantity of clock pulses and providing an inhibit signal to said pulse generator means after a predetermined quantity of clock pulses is counted, the time interval between said gate start pulse and said inhibit signal defining a gated time interval;
   shift register means coupled to said comparing means and said pulse generator means for sampling and shifting the output signal responsive to the receipt of each said clock pulse, thereby providing digital signals at predetermined time increment during a gated time interval;
   resetting means coupled to said shift register means for sensing said digital signals and providing a reset signal when said echo signal fails to exceed the amplitude level of said reference signal during a gated time interval, and
   microprocessor means coupled to said reference signal generating means, said counter means, said shift register means and said resetting means for:
   (a) storing said digital signals from said shift register in time increment responsive relation,
   (b) resetting said counter means and either
   (c) causing said reference signal generating means to incrementally vary the amplitude level of said reference signal in the absence of said reset signal or
   (d) causing said reference signal generating means to establish the initial value of the amplitude level of said reference signal responsive to the receipt of said reset signal.

16. The apparatus as set forth in claim 15, said microprocessor means summing said digital signals in time increment responsive relation.

17. The apparatus as set forth in claim 16, said initial value of the amplitude level of said reference signal being a base level and said varying the amplitude level comprising incrementally increasing the amplitude level.

18. The apparatus as set forth in claim 16, said initial value of the amplitude level of said reference signal being a maximum amplitude level and said varying the amplitude level comprising incrementally decreasing the amplitude level.

19. An apparatus as set forth in claim 14, said microprocessor including means for summing said stored digital signals in time increment responsive relation.

* * * * *